(12) United States Patent
Santore et al.

(10) Patent No.: US 7,752,931 B2
(45) Date of Patent: Jul. 13, 2010

(54) NANOPATTERNED SURFACES AND RELATED METHODS FOR SELECTIVE ADHESION, SENSING AND SEPARATION

(75) Inventors: Maria M. Santore, Sunderland, MA (US); Natalia Kozlova, Belmont, MA (US)

(73) Assignee: University of Massachusetts, Boston, MA (US)

(*) Notice: Subject to any disclaimer, the term of this patent is extended or adjusted under 35 U.S.C. 154(b) by 547 days.

(21) Appl. No.: 11/592,454

(22) Filed: Nov. 3, 2006

(65) Prior Publication Data

US 2007/0111198 A1    May 17, 2007

Related U.S. Application Data

(60) Provisional application No. 60/732,941, filed on Nov. 3, 2005.

(51) Int. Cl.
| | |
|---|---|
| G01N 15/00 | (2006.01) |
| G01N 15/10 | (2006.01) |
| G01N 13/00 | (2006.01) |
| G01N 27/60 | (2006.01) |
| G01N 27/62 | (2006.01) |

(52) U.S. Cl. .................... 73/866.5; 73/28.01; 73/28.02; 73/61.71; 73/104; 324/71.1; 324/452; 324/464; 977/953; 977/956

(58) Field of Classification Search ..... 73/28.01–28.02, 73/61.62, 61.71–61.72, 104, 866.5; 324/71.1, 324/452, 464; 435/4, 287.1; 977/953, 956–957
See application file for complete search history.

(56) References Cited

U.S. PATENT DOCUMENTS

| | | | | |
|---|---|---|---|---|
| 6,143,247 | A * | 11/2000 | Sheppard et al. | ............... 422/63 |
| 6,319,469 | B1 * | 11/2001 | Mian et al. | ..................... 422/64 |
| 6,999,703 | B2 * | 2/2006 | Hays | .......................... 399/252 |
| 7,291,427 | B2 * | 11/2007 | Kawamura et al. | ............ 430/15 |
| 7,364,898 | B2 * | 4/2008 | Peters et al. | .......... 435/287.1 X |
| 7,517,656 | B2 * | 4/2009 | Martin et al. | ......... 435/287.1 X |
| 7,608,419 | B2 * | 10/2009 | Ponce | ................. 435/287.1 X |
| 2004/0184840 | A1 * | 9/2004 | Hays | .......................... 399/252 |
| 2006/0183223 | A1 | 8/2006 | King et al. | |
| 2009/0124016 | A1 * | 5/2009 | Santore et al. | ................. 436/86 |
| 2009/0155800 | A1 * | 6/2009 | Hong et al. | ............. 977/953 X |
| 2009/0197297 | A1 * | 8/2009 | Murray et al. | ........ 435/287.1 X |

OTHER PUBLICATIONS

Shin, Y; Roberts, JE; and Santore, MM; The Relationship Between Polymer/Substrate Charge Density and Charge Overcompensation by Adsorbed Polyelectrolyte Layers; Journal of Colloid and Interface Science, Mar. 2002, 220-230, vol. 247, No. 1., abstract only.

Adamczyk, Z; Weronski, P; and Musial, E; Colloid Particle Adsorption at Random Site-(Heterogeneous) Surfaces; Journal of Colloid and Interface Science, Apr. 2002, 67-75, vol. 248, No. 1.

(Continued)

*Primary Examiner*—Thomas P Noland
(74) *Attorney, Agent, or Firm*—Reinhart Boemer Van Deuren s.c.

(57) ABSTRACT

A surface comprises a surface member and a plurality of components thereon. Such heterogenous surface compositions and configurations, related systems and methods for sensing particle or analyte interaction therewith can selectively and/or differentially interact with a range of particles/analytes, in lieu of specific molecular sensor-analyte interactions for each particle.

15 Claims, 10 Drawing Sheets

OTHER PUBLICATIONS

Kozlova, N; and Santore, MM; Manipulation of Micrometer-Scale Adhesion by Tuning Nanometer-Scale Surface Features; Langmuir, 2006, 1135-1142, vol. 22, No. 3, (published on Web Dec. 21, 2005).

Narasipura, S.D.; Wojciechowski, J.C.; Duffy, B.M.; Liesveld, J.L.; King, M.R.; Purification of CD45+ hematopoietic cells directly from human bone marrow using a flow-based P-selectin-coated microtube. Am. J. Hematol. 83:627-629, 2008.

Kalasin, S.; Santore, M.M.; Hydrodynamic Crossover in Dynamic Microparticle Adhesion on Surfaces of Controlled Nanoscale Heterogeneity. Langmuir, 24 (9), 4435-4438, Mar. 2008.

Wojciechowski; J.C.; Narasipura, S.D.; Charles, N.; Mickelsen, D.; Rana, K.; Blair, M.L.; King, M.R; Capture and enrichment of CD34-positive haematopoietic stem and progenitor cells from blood circulation using P-selectin in an implantable device. Blackwell Publishing, Ltd., British Journal of Haematology, 140, 673-681, Jan. 2008.

Narasipura, S.D.; Liesveld, J.L.; Wojciechowski, J.C.; Charles, N.; Rosell, K.; King, M.R.; Enrichment of CD34+ Hematopoietic Stem and Progenitor Cells From Human Bone Marrow Using a P-Selectin-Coated Microtube. Blood (ASH Annual Meeting of Abstracts) 2007, 110: Abstract 1219. © 2007 American Society of Hematology.

Narasipura, S.D.; Wojciechowski; J.C.; Charles, N.; Mickelsen, D.; K.; Blair, M.L.; King, M.R.; Capture and Enrichment of CD34-Positive Haematopoietic Stem and Progenitor Cells from Blood Circulation Using P-Selectin in an Implantable Device. Blood (ASH Annual Meeting of Abstracts) 2007, 110: Abstract 4918. © 2007 American Society of Hematology.

Nagrath, S.; Sequist, L.V.; Maheswaran, S.; Bell, D.W.; Irimia, D.; Ulkus, L.; Smith, M.R.; Kwak, E.L.; Digumarthy, S.; Muzikansky, A.; Ryan, P.; Balis, U.J.; Tompkins, R.G.; Haber, D.A.; Toner, M.; Isolation of rare circulating tumour cells in cancer patients by microchip technology. Nature, vol. 450, 20/27 Dec. 2007, pp. 1235-1241.

Santore, M.M.; Kozlova, N.; Micrometer Scale Adhesion on Nanometer-Scale Patchy Surfaces: Adhesion Rates, Adhesion Thresholds, and Curvature-Based Selectivity. Langmuir, 23 (9), 4782-4791, Mar. 2007.

Duffadar, R.D.; Davis, J.M.; Interaction of micrometer-scale particles with nanotextured surfaces in shear flow. Journal of Colloid and Interface Science, 308 20-29, Jan. 2007.

Kozlova, N.; Santore, M.M.; Manipulation of Micrometer-Scale Adhesion by Tuning Nanometer-Scale Surface Features. Langmuir, 2006, 22 (3), 1135-1142, published on Web Dec. 2005.

Giang, U.B.T.; King, M.R.; Delouise, L.A.; Microfabrication of Bubbular Cavities in PDMS for Cell Sorting and Microcell Culture Applications. Journal of Bionic Engineering (2008), vol. 5, No. 4, pp. 308-316.

Lee, D.; King, M.R.; Microcontact Printing of P-Selectin Increases the Rate of Neutrophil Recruitment Under Shear Flow. Biotechnol. Prog. 2008, vol. 24, No. 5, pp. 1052-1059.

Shao, N.; Wickstrom, E.; Panchapakesan, B.; Nanotube-antibody biosensor arrays for the detection of circulating breast cancer cells. Nanotechnology 19, (2008) 465101, pp. 1-11.

Ehrhart, J.C.; Bennetau, B.; Renaud, L.; Madrange, J.P.; Thomas, L.; Morisot, J.; Brosseau, A.; Allano, S.; Tauc, P.; Tran, P.L.; A new immunosensor for breast cancer detection using antibody-coated long alkylsilane self-assembled monolayers in a parallel plate flow chamber. Biosensors and Bioelectronics 24 (2008) 467-474.

Duffadar, R.D.; Davis, J.M.; Dynamic adhesion behavior of micrometer-scale particles flowing over patchy surfaces with nanoscale electrostatic heterogeneity. Journal of Colloid and Interface Science 326 (2008) 18-27.

Saliba, A.; Microfluidic Magnetic Cell Sorting System for CTC Detection and Typing. Anticancer Research 28: 3350-3351, Oct. 2008.

Karnik, R.; Hong S., Zhang, H.; Mei, Y. Anderson, D.G.; Karp, J.M.; Langer; R., Nanomechanical Control of Cell Rolling in Two Dimensions through Surface Patterning of Receptors, Nano Letter., 2008, 8 (4), 1153-1158; publication date (web): Mar. 6, 2008.

* cited by examiner

Figure 10A
Figure 10B
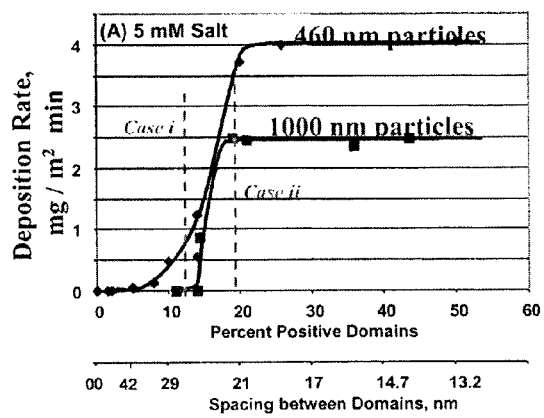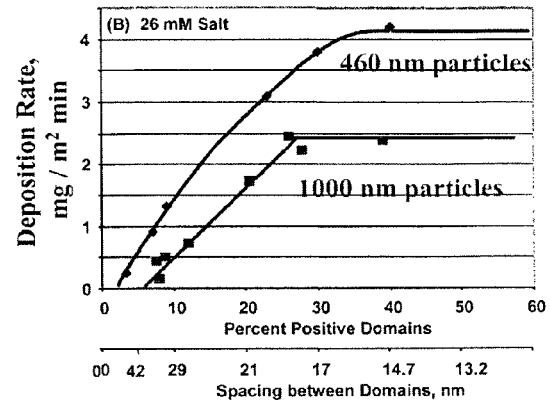
Figure 11
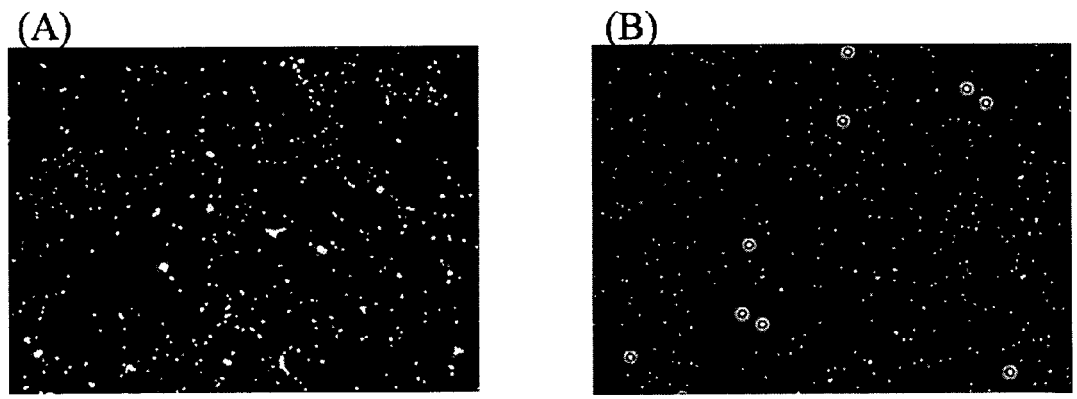

# NANOPATTERNED SURFACES AND RELATED METHODS FOR SELECTIVE ADHESION, SENSING AND SEPARATION

This application claims priority benefit from prior provisional application Ser. No. 60/732,941 filed Nov. 3, 2005.

The United States government has certain rights to this invention pursuant to Grant Nos. CTS-0234166 and CTS-0242647 from the National Science Foundation to the University of Massachusetts.

BACKGROUND OF THE INVENTION

Nanometric surface design has been a research focus over the past decade, with a variety of concepts and methods developed. Most produce features with a size scale greater than 100 nm (e.g., standard photolithography, microcontact printing and/or with regularity interference methods). Such methods are labor or equipment intensive. Consider, for instance, the fabrication of a lithographic mask for the fabrication of a complex mold to produce stamps for microcontact printing. Scribe-type methods (AFM-writing, e-beam lithography, with nanometric resolution) are not only both labor and equipment intensive, but are also substantially limited in terms of surface chemistry. Only recently have interference methods been applied to e-beam lithography, but at the cost of production limited only to regular patterns.

Concurrently, increasing effort has been made to design and fabricate surfaces with selective properties, for use in conjunction with tissue scaffolds, sensors, smart adhesives, separation media, etc. Selectivity has been most often achieved, borrowing directly from biology, by the covalent attachment of biomolecular fragments (both polypeptide and DNA), and the passivation of remaining surface area. The resulting surfaces bind target molecules, often in micron and slightly submicron patterns that form the basis for array devices. While there is much to be gained by direct incorporation of biomolecules or biomimetic analogs, such systems tend to be technically narrow and limited to detection of specific sensor-analyte chemical or immunological interactions. Incorporation of biological molecules or fragments also can limit device lifetime and usage conditions, since biological molecules are often readily degraded.

Most patterned surfaces made by the foregoing techniques are designed to store information or provide arrays for addressable multi-element sensing. Wherein such arrays are used for sensor elements, biological molecules (DNA, proteins and antibodies) are placed in various parts of the array, thereby imparting specificity to each array element. Informational density and sensitivity can be but are not necessarily promoted by decreasing sensor size and/or adding more or different sensor elements. As a result, improved detection continues to present on-going fabrication challenges.

SUMMARY OF THE INVENTION

In light of the foregoing, it is an object of the present invention to provide selective separation and sensing compositions and/or articles and methods for the use and/or assembly, thereby overcoming various deficiencies and shortcomings of the prior art, including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide heterogeneous surface compositions, relative amounts of components A and B, surface lengthscale for distribution of A on B, lengthscale for the size of A domains and/or chemical nature of A and B, for selective interaction of particles or analytes exposed thereto, such heterogeneity as can be considered in terms of such selectivity at least in part related to particle/analyte size, and/or local curvature.

It can be another object of the present invention to provide such a composition, surface and/or related method to selectively distinguish particles/analytes in a size range from less than about 50 nanometers to greater than about 5 microns, without limitation as to the chemical characteristics of any such particle/analyte.

It can be another object of the present invention to provide any such composition, surface, system and/or related method using spatial dimension, spatial configuration and/or density of corresponding surface components to effect or control selective separation or detection.

It can be another object of the present invention to provide a heterogeneous or patterned surface, for use with a related system or method, robust to pH, temperature and other environmental factors, and which selectively interacts with target particles or analytes over those outside a predetermined size range or physical/chemical profile characteristic.

It can be another object of the present invention to provide a heterogeneous surface, system or related method, selectively and/or differentially interactive with a range of particles/analytes, each with its own recognition pattern, in lieu of a specific sensor-analyte chemical interaction for each particle.

Other objects, features, benefits and advantages of the present invention will be apparent from this summary and the following descriptions of certain embodiments, and will be readily apparent to those skilled in the art having knowledge of various separation/sensing techniques. Such objects, features, benefits and advantages will be apparent from the above as taken into conjunction with the accompanying examples, data, figures and all reasonable inferences to be drawn therefrom, alone or with consideration of the references incorporated herein.

In part, this invention can comprise a method for particle sensing and/or of using a spatial surface configuration for selective particle interaction. Such a method can comprise (1) providing a heterogeneous surface comprising a surface member and a plurality of components thereon, such components spaced about said surface and having an average surface density, the heterogeneity comprising different interactions of the surface member and the spaced components with a particle or analyte exposed thereto; (2) exposing a particle to the heterogeneous surface; and (3) sensing different interactions of the particle with the heterogeneous surface, selective for such a particle.

While various interactions, e.g., physical or chemical, can be utilized in conjunction with this method, in certain embodiments, the heterogeneity on the surface member can comprise different electrostatic interactions with a particle of a net charge, whereby the surface member and the spaced components thereon have opposed electrostatic charges. In particular, the spaced components can, themselves, have a surface charge density or number at least partially sufficient for selective particle interaction; and particle ionic strength can be further varied, as determined, to alter or modify selectivity. Regardless, such surface components can also comprise an average spatial density at least partially sufficient for selective particle interaction. Such density can be varied as may be required for enhanced selectivity of a specific particle/ analyte. Accordingly, charge density and/or spatial density can be utilized, modified and/or altered for selective interaction with a first particle of a first dimension, such selectivity over a second particle with a second, different radial dimension and/or localized surface radius of curvature. Particle displacement can provide such a surface for subsequent or repetitious exposure and sensing.

Without limitation, particle/analyte sensing can comprise a rate of adhesion to the heterogeneous surface and one or more other interactive signatures including but not limited to rolling, skipping and arrest, such interactions as would be understood by those skilled in the art. Accordingly, sensing can comprise one or more signatures or a sequence of signatures for a specific particle/analyte interaction, whereby such a method can be used for selective sensing upon exposure of a particle mixture to the heterogeneous surface. Removal of adhered/interacted particles permits use of the surface for subsequent exposure and sensing.

In part, this invention can also be directed to a system for selective particle sensing. Such a system can comprise a heterogeneous surface comprising a surface member and a plurality of components thereon, such components spaced about and having a surface density, with the heterogeneity comprising different interactions of the surface member and of the spaced components with a particle/analyte exposed thereto. As discussed elsewhere herein, various surface heterogeneities and different interactions can be utilized; however, in certain embodiments, competing electrostatic interactions with a particle of net charge can be provided using a surface member having a charge opposite to the surface components thereon. In certain embodiments a surface member can have a net negative charge, and a spaced component can have a net positive charge. Such an embodiment is available through deposition of one of several commercially available cationic polymers onto a silica surface at levels below those corresponding to surface saturation (e.g., without limitation, up to about 50%). As discussed elsewhere herein, component spacing can be optimized to provide an interactive threshold of such a heterogeneous surface for a specific particle/analyte. In certain non-limiting embodiments, components spaced from about 15 nanometers to about 60 nanometers can be used to sense micron-dimensioned particles. In certain other embodiments, components spaced from about 15 nanometers to about 30 nanometers for selective particle sensing. Such spacing or density can be varied, separately or in conjunction with the size and/or charge density of the spaced components. Accordingly, as described more fully below, such a system can be designed and used to selectively sense particles of a given dimension or chemical/physical characteristic.

In part, this invention can also be directed to a method for determining particle signature. Such a method can comprise (1) providing a heterogeneous surface comprising a surface member and a plurality of components thereon, such components spaced about and having an average density on the surface member, with the surface heterogeneity comprising differential interactions of the surface member and spaced components with an exposed particle and selectively interactive therewith; (2) exposing one or more known particles to the heterogeneous surface; (3) sensing interactions of the known particles with the heterogeneous surface; and (4) determining one or more signature interactions, in recognition of each known particle. Such signature(s), once determined, can be used for purposes of comparison with a signature of an unknown particle/surface interaction to identify the unknown particle. As mentioned above and discussed more fully below, surface heterogeneity can give rise to various different or competitive surface interactions with an exposed particle. Likewise, in certain embodiments, a surface member and spaced components thereon can comprise domains of opposed charges for different electrostatic interaction with a particle having a net charge. Charge density, surface spacing, spatial density and/or domain size can be varied for selective or optimal interaction of such a heterogeneous surface with a particle/analyte of a given dimension or curvature. Such interactive signatures can comprise adhesion, arrest, rolling, skipping and/or other interactive signatures recognized by those skilled in the art, whereby a interactive pattern can ascertained, in recognition of the known particle. As such, exposure of a second or unknown particle and comparison with a recognized interactive signature can be used to determine or assess identity of a second/unknown particle.

BRIEF DESCRIPTION OF THE DRAWINGS

FIGS. 10A-B. Comparative adhesion rates of silica particles onto heterogeneously electrostatic surfaces, as a function of particle size and domain density. (A) ionic strength is 5 mM. (B) ionic strength is 26 mM.

FIGS. 11A-B. (A) optical micrograph of the charge-wise heterogeneous surface from case i of FIG. 10A, after exposure to a flowing suspension containing fluorescent-core 460 nm silica particles (65 wt %) and 1 μm non-fluorescent silica particles (35 wt %); and (B) optical micrograph of the charge-wise heterogeneous surface from case ii control of FIG. 10A.

BRIEF DESCRIPTION OF CERTAIN EMBODIMENTS

Description of Heterogeneous Surface

Figure 1:
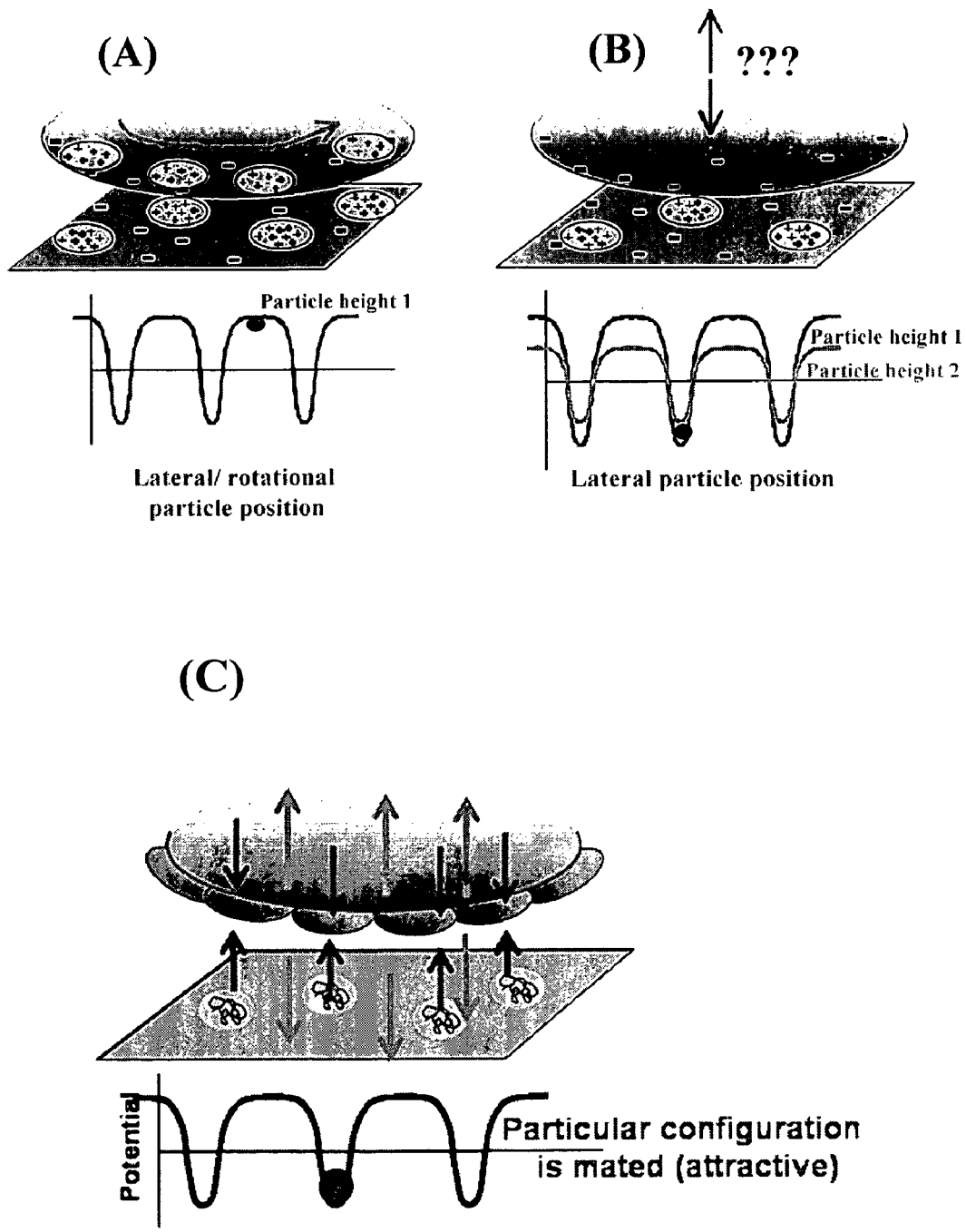
FIGS. 1A-C. Schematic illustrations (not to scale) of a charge-based heterogeneous surface and spatially varying interactions with three types of potential analyte particles in A, B, and C. On the heterogeneous surface of such non-limiting embodiments, the positive domains can be on the order of 10 nm in diameter and their average spacing can vary from zero to over 100 nm, and particle size can range from less than about 200 nm to greater than several microns.

Without limitation to any one theory or mode of operation, various aspects and features relating to certain embodiments of this invention can be considered in conjunction with FIGS. 1A-C. In FIG. 1B, a negative micron-scale sphere interacts with a negative surface carrying patches of multiple positive charges, where the patches are substantially smaller than the sphere. At any position, the sphere experiences both attractions and repulsions at different points on its surface. The sphere is currently in an attractive well, and translation of the sphere over the surface results in a height-dependent spatially varying potential. A different sized sphere would experience a different proportion of attractions and repulsions such that the heterogeneous surface will attract some particle sizes better than others. In the experimental scenario of FIG. 1B, a relatively smooth negatively charged particle interacts with an electrostatically heterogeneous surface presenting attractive (positive) domains on an otherwise repulsive (negative) surface, where the domains are small relative to the particle size. Lateral variations in surface charge (the heterogeneous domains) attract or repel the sphere, depending on its position in the x, y, and z directions. Thus the approaching sphere experiences a potential energy landscape. In FIG. 1B, the particle experiences this landscape by translating across the surface. This situation is similar to the more classical pattern-recognition situation, in FIG. 1A where, with a pattern on both sides of the interface, attractions and repulsions result from particle translation and rotation. The surface of the micron-scale sphere illustrated in FIG. 1A contains multi-charged positive domains. Depending on the size and spacing of the positive domains on the sphere relative to those on the surface, pattern recognition and adhesion, with various dynamic signatures, may or may not be achieved, thus producing selectivity. In the example shown, the size and spacing of the domains on the sphere are similar to those on the heterogeneous planar surface giving rise to the possibility of adhesion. The sphere is currently in a repulsive maximum and translation or rotation will cause the potential to vary. A slight rotation or translation from the current position would move the sphere to a local minimum, producing adhesion. If the patch distribution on the sphere were out of registry with that on the plane, a more complicated potential with weaker attractions would result. Likewise in FIG. 1C, a similar affect may be observed for a particle with surface roughness of a particular lengthscale, but a relatively uniform charge distribution, in this case negative. Here the analyte is not a sphere, but an aggregate of smaller primary spheres, carrying only negative charge. In addition to the lengthscale of the overall analyte particle, there is a lengthscale of the small primary spheres making up the aggregate. In this example, the small sphere lengthscale is in registry with the lengthscale implicit in the heterogeneous surface, giving rise to attractions. A different size primary particle in the aggregate would break this registry and reduce attractions and adhesion.

As demonstrated below, tuning the interfacial features of FIG. 1A allows manipulation of adhesion dynamics, including an adhesion threshold. Further, the adhesion dynamics of particles such as those in FIG. 1C (where large particles are aggregates of smaller primary particles, imparting a surface roughness lengthscale) are distinct from that of smooth particles with the same overall size and surface charge density as that in FIG. 1A. Adhesion or sensing occurs with pattern feature density above the threshold, but not below it. Utilizing this invention, a selective behavior is observed for the system in FIG. 1A, one more typically associated with the classical pattern recognition scenario in FIG. 1B. Selectivity is also observed for the system in FIG. 1C.

Implementing such features, this invention can be demonstrated using the interactions between micron-scale (460 nm) silica particles and planar surfaces containing randomly-arranged 11-nanometer electrostatically adhesive patches of varied density (with the remaining surface area being electrostatically repulsive towards the particles). Rather than AFM, colloidal probe, or surface forces methods, particle deposition from gently flowing solution was employed to assess the interactions from a practical perspective and to demonstrate pattern recognition-like, selective features of the interactions. Adhesion rates were observed as a function of the domain density, and a certain range of surface conditions were found to promote adhesion, much like the concept of interfacial pattern recognition.

Representative of this invention, and demonstrating but one utility thereof, heterogeneous planar surfaces were made by adsorbing controlled amounts of a cationic polyelectrolyte, poly(dimethylaminoethyl methacrylate), pDMAEMA, onto the negative surface of an acid washed microscope slide. At high coverages approaching saturation, adsorbed polymer layers typically form a dense carpet over a surface, but at lower coverages, individual chains can be distinguished by the right techniques. In this example, the individual polymer chains comprise the positive domains. The domains roughly can be envisioned as round with order 10 nm diameter, but flat to the surface and randomly placed, based on a large bank of data collected in the literature. (See, Shin, Y.; Roberts, J. E.; Santore, M. M. *Macromolecules* 2002, 35, 4090-4095; Shin, Y. W.; Roberts, J. E.; Santore, M. M. *Journal of Colloid and Interface Science* 2002, 247, 220-230; Hansupalak, N.; Santore, M. M. *Macromolecules* 2004, 37, 1621-1629; Hansupalak, N.; Santore, M. M. *Langmuir* 2003, 19, 7423-7426.) Roundish domains (rather than substantially elongated or extended chains) would be expected in the limit where small amounts (isolated chains) of pDMAEMA adsorb to the silica surface, because under typical adsorption conditions (which include an ionic strength of 0.026 M, and gentle shearing flow) pDMAEMA is a coil rather than an extended chain in free solution. The fast adsorption rate and the strong (irreversible) adsorption energetics minimize the potential for substantial reconformations of segments after they contact the surface, so that the free coil conformation should be reflected at least roughly by the adsorbed footprint or domain size. (See, Irurzun, I. M.; Matteo, C. L. Macromolecular Theory and Simulations 2001, 10, 237-243; Hoogeveen, N. G.; Stuart, M. A. C.; Fleer, G. J. Journal of Colloid and Interface Science 1996, 182, 133-145; Hansupalak, N.; Santore, M. M. Macromolecules 2004, 37, 1621-1629.)

The particular pDMAEMA utilized had a molecular weight of 31,300 (200 monomers) and a polydispersity of 1.1. A hydrodynamic coil radius, $R_H$, of 4.5 nm measured by dynamic light scattering approximates the radius of gyration, $R_g$ to first order for these coils in solution. The adsorbed chain footprint is expected to be similar, with the patch diameter approximated by the free coil end-end distance, $6^{1/2}R_g$, 11 nm. Since pDMAEMA is a weak polyelectrolyte its protonation is pH-dependent: At the pH of 6.1 in this study, pDMAEMA is 70% protonated in free solution, but because of the relatively dense spacing of these underlying backbone charges, counterion condensation reduces the net backbone charge to a spacing approaching the Bjerrum length of 0.7 nm, or 74 net positive charges/chain. (See, Shin, Y. W.; Roberts, J. E.; Santore, M. M. Journal of Colloid and Interface Science 2002, 247, 220-230; Shin, Y. W.; Roberts, J. E.; Santore, M. Journal of Colloid and Interface Science 2001, 244, 190-199.)

The individually adsorbed DMAEMA chains would be expected to produce relatively flat (order 1 nm thick) domains, per conventional wisdom for the adsorption of substantially-charged polyelectrolytes. Indeed, NMR studies, at conditions relevant to this study, found adsorbed pDMAEMA chains to lie flat to the surface: At pH's of 7 and below, saturated layers (with coverages of 0.6 mg/m$^2$) are 80% trains (the part of the chain that contacts the surface), and no more than 20% loops and tails. At coverages below 0.1 mg/m$^2$, where interesting adhesion kinetics of silica particles were found in the current work, the adsorbed polymer is 100% trains within detectable limits. This means that the polymer domains are relatively flat to the surface, extending only the thickness of the backbone (order 1 nm) into solution. Domain arrangement on the collector surfaces is expected to be random, especially at low domain coverages when chain spacing exceeds the Debye length. Aggregation or clustering of adsorbed chains is improbable since positive backbone charge causes interchain repulsion. Additionally, no aggregation is observed in bulk at pH 6 over a broad range of ionic strength.

A concern in using adsorbed polymer as a component of random surface patterning is that it stays adsorbed to the underlying planar surface. In this work pDMAEMA was employed at pH 6.1 where shown that it does not desorb or exchange with material from solution over a period of days. While salt often facilitates polyelectrolyte desorption, in this system at pH 6 or 7 it has almost no effect on the adsorbed amount, presumably due to dense backbone charging. Because pDMAEMA chains are so immobile against desorption or self exchange with other pDMAEMA chains, a low lateral mobility of these chains would also be expected—when encountered by colloidal particles—to promote steady position. In fact, controls employing fluorescent pDMAEMA demonstrated complete domain retention on exposure to particles.

Another feature of the heterogeneous surface of this invention is its electrostatic landscape. It is well known that saturated layers of polyelectrolytes with sufficient backbone charge can reverse the underlying substrate charge. This behavior can enable multilayer structures containing negatively- and positively-charged polyelectrolytes. Indeed saturated pDMAEMA layers on silica, in a pH range of the sort described herein, are known to completely reverse the underlying silica charge. While the interesting adhesion threshold region in this invention corresponds to sufficiently low pDMAEMA coverages to produce isolated adsorbed coils, the region in the vicinity of each coil would be expected to be positively charged. Indeed, the concept that single chains can contribute electrostatic domains is well established in the cationic flocculant literature. When adsorbing chains are too short to induce bridging flocculation, addition of small amounts of densely positively charged polymer to negatively charged colloids can induce flocculation by electrostatic attraction of the positive domains adsorbed on one sphere to the negative bare surface of a colliding particle.

Figure 2:
FIG. 2. Schematic illustration of a positively charged domain. The representation on the left shows the adsorbed polycation (single chain) while that on the right emphasizes the charge distribution and downplays the backbone conformation.

In the literature, the electrophoretic mobility of pDMAEMA adsorbed on silica spheres (a model approximating planar surfaces herein) was linear in the adsorbed amount of pDMAEMA, over the full range of pDMAEMA coverages from bare silica to saturated pDMAEMA layers. (Shin, Y. W.; Roberts, J. E.; Santore, M. M. *Journal of Colloid and Interface Science* 2002, 247, 220-230.) That observation indicates that each adsorbing chain, from the first chain to adsorb onto a bare silica surface to the last to incorporate into a saturated layer, brings the same net charge to the interface. In the dilute surface limit of just a few pDMAEMA chains on a relatively bare silica surface, positive charge should be localized in the vicinity of the adsorbed chains. Measurements of the electrophoretic mobility, and titrations of the charge in the polymer solutions and colloidal dispersions led to calculations of the charge associated with each adsorbed chain. At pH 6, adsorbing pDMAEMA releases sodium ions from silica's double layer and promotes further ionization of surface silanols, which locally increases the underlying negative charge on the silica. Even with this charge regulation, however, each adsorbing pDMAEMA chain brings +28 charges to the surface (through the combined processes of adsorption, counterion release, and silica charge regulation). (The electrokinetically measurable charge is lower due to counterions present.) By comparison, the silica bare silica surface charge density is 0.16-ve charges/nm$^2$ at pH 6. Accordingly, a surface can be considered by the scenario in FIG. 2, which includes ~11 nm domains with 28 positive charges each, in a sea of negative charge with average density $-0.16/nm^2$. In this work the domain density is varied to give interesting adhesion with particles in solution.

Demonstration of Adhesion Rate Control

As a reference point in characterizing the adhesion rates of colloidal particles, the deposition of silica particles was examined on microscope slides carrying saturated (full) layers of pDMAEMA, with a coverage of 0.45 mg/m$^2$. These polymer layers were adsorbed at pH 6.1 I=0.026M and, at these conditions, the underlying silica surface charge is completely reversed. In other words, the negative silica surface is made positive. Such positively charged surfaces should be strongly adhesive towards negatively charged particles in solution. As described below and in the following examples, silica spheres exhibited transport-limited adhesion to full pDMAEMA layers, confirming the absence of an energy barrier between the negative particles and a relatively uniform positive planar surface. The confirmation of the transport-limited adhesion rate onto positive surfaces carrying full pDMAEMA layers demonstrates the quantitative accuracy of the adhesion rate measurement and confirms our understanding of principle in the uniform surface (particle-surface attractions) regime.

Figure 3:
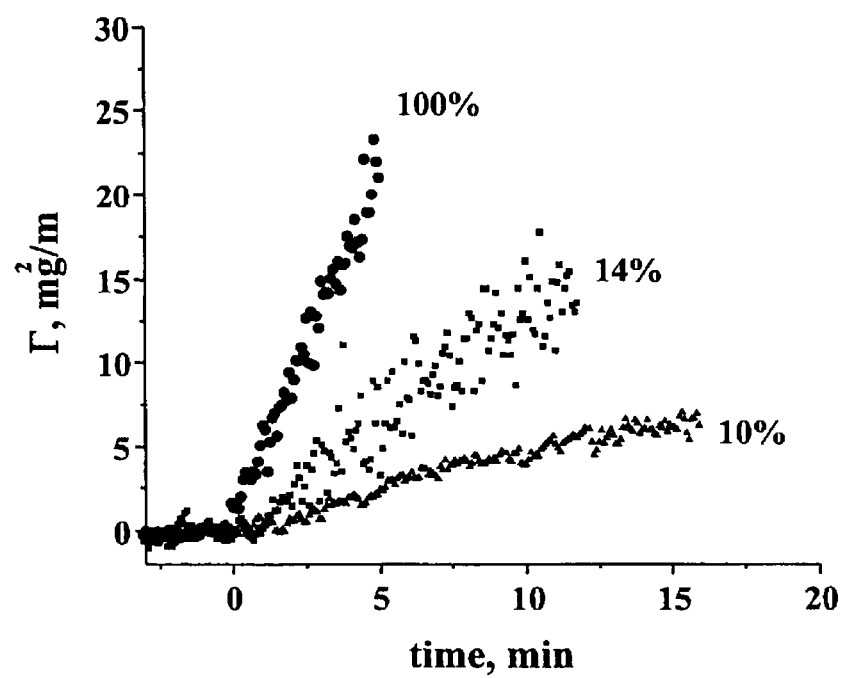
FIG. 3. Limiting low-coverage particle (460 nm silica spheres) adhesion kinetic data at 3 different positive domain (pDMAMEA) densities (10%, 14%, 100%) on a planar collector (heterogeneous surface). Ionic strength is 0.005M.

FIG. 3 shows initial adhesion kinetics of 460 nm silica particles on planar surfaces carrying different amounts of positive domains: 10%, 14%, and 100%. Percent-domain loading is arbitrarily defined relative to the saturated pDMAEMA layer of 0.45 mg/m². Since the interfacial charge is linear in the amount of pDMAEMA deposited, and since at pH 6 the saturated pDMAEMA surface almost exactly overcompensates the underlying silica charge, 50% domains corresponds to a planar surface with net zero charge, even though the substantial charge is distributed between polymer-rich and silica-rich regions of the surface. The "percent" description of domain loading is not defined in terms of surface area though the result is actually close in this example. At a saturation coverage of 0.45 mg/m², the apparent footprint of each chain is 87 nm² (corresponding to a disk with diameter 10.5 nm). This footprint diameter is in good agreement with the 11 nm diameter light scattering estimate from the free coil size. While in reality adsorbed polymer layers are typically thought of as entangled carpets of chains, as the surface is made more dilute, individual coils should ultimately become distinguishable (by the right experimental probes). Results are especially interesting in the dilute limit where the question of adsorbed chain identity is not blurred by the possibility of chain overlap on the surface.

In FIG. 3, particle adhesion onto a surface containing 100% domains (a saturated pDMAEMA layer) proceeds at the transport limited rate per the previous discussion, indicating fundamentally fast underlying adhesion kinetics between the spheres and the collector. With 14% and 10% domains, however, the deposition rate becomes increasingly slower, indicating a reduction in the fundamental sticking rate of particles as they approach the interface. The finite adhesion rate constants associated with these heterogeneous surfaces can be thought to reflect an energy barrier resulting from competing attractive and repulsive forces acting on a single particle, and the fact that particles approaching the interface in a locally negative region of the collector will have a greater probability of rejection than those more directly approaching the positive domains.

Figure 4:
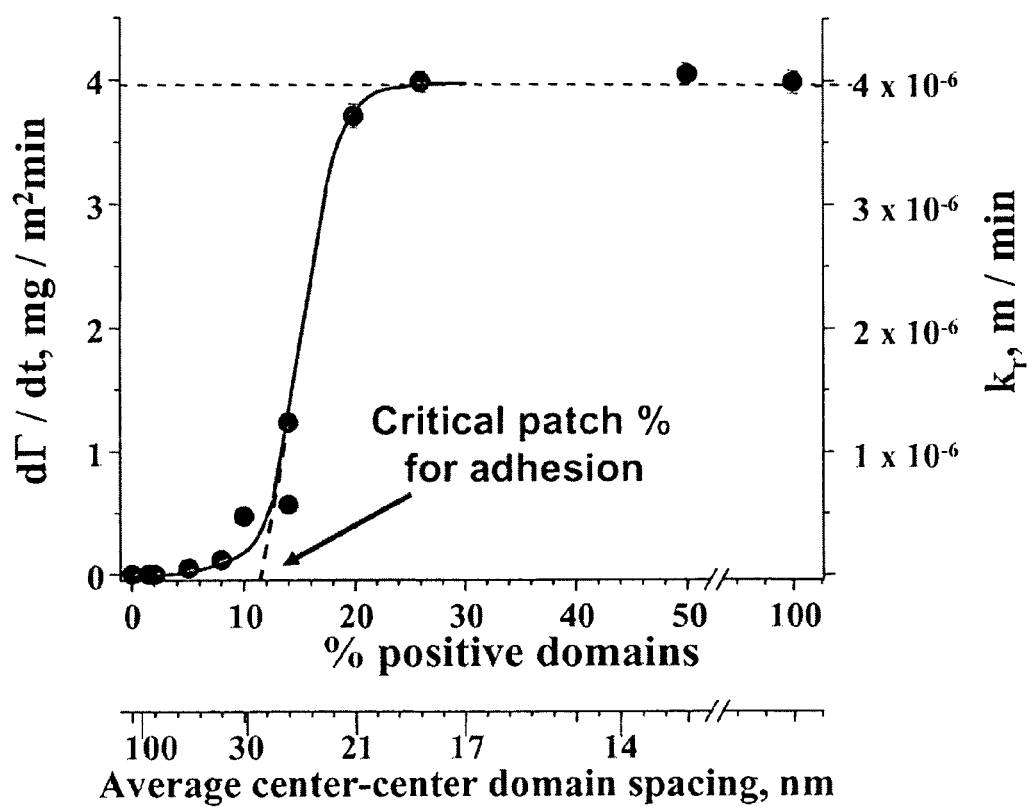
FIG. 4. Adhesion rates of 460 nm silica particles as a function of domain density for I=0.005M.

FIG. 4 summarizes the data in FIG. 3 and similar runs for a bulk solution concentration of 0.1 wt % particles and an ionic strength of 0.005M. The x-axis is linear in the pDMAEMA loading on the collector, represented as "% domains"; and a second x-axis shows the average spacing between the centers of the pDMAEMA coils (domains). The left y-axis shows the particle adhesion rate while the right y-axis translates this to a set of adhesion rate constants. Several interesting features appear, starting on the right hand side of the graph (high or dense domain loading on the collector) where the transport limited particle deposition rate persists for a substantial range of relatively high positive domain densities: Even when the surface has substantial negative regions, particles approaching the planar collector can quickly find positive regions of the surface where they adhere. This is the case at 50% domain density, where transport-limited deposition occurs even though the surface is net neutral, and down to about 25% domain loading where the surface carries a substantial net negative charge and the average center-center domain spacing is about 19 nm. In this large transport-limited regime of particle deposition, from 25-100% domain loading, adhesion of the 460 nm silica particles was observed to be irreversible. That is, like the data in FIG. 3, the particles were not displaced from the surface during buffer flow subsequent to their initial deposition. The particle adhesion rate only becomes noticeably slow (relative to the transport limit) for average positive domain spacings of 20 nm or more.

As the average spacing between the positive domains is increased and as the surface becomes increasingly net negative, the particle adhesion rate decreases. Ultimately the particle adhesion rate approaches zero, at a finite value of the average domain spacing, near 28 nm. It is notable that the sloping branch of the data in FIG. 4 does not insect the origin, but rather defines a threshold interfacial condition for adhesion. From another perspective, the fact that the data miss the origin suggest that one domain alone on a negative surface is not sufficient to trap and hold a particle (otherwise there would be finite particle accumulations and measurable rates for all patch loadings greater than zero). Hence, adhesion of particles in the methods and systems of this invention is believed to rely on spatial fluctuations in the domain placement on the surface: particles tend to selectively adhere to regions of the surface containing a higher than average density of positive domains. Accordingly, the nanometric features of this invention can be used for recognition of analytes or components 100 times larger than the domain size.

Figure 12:
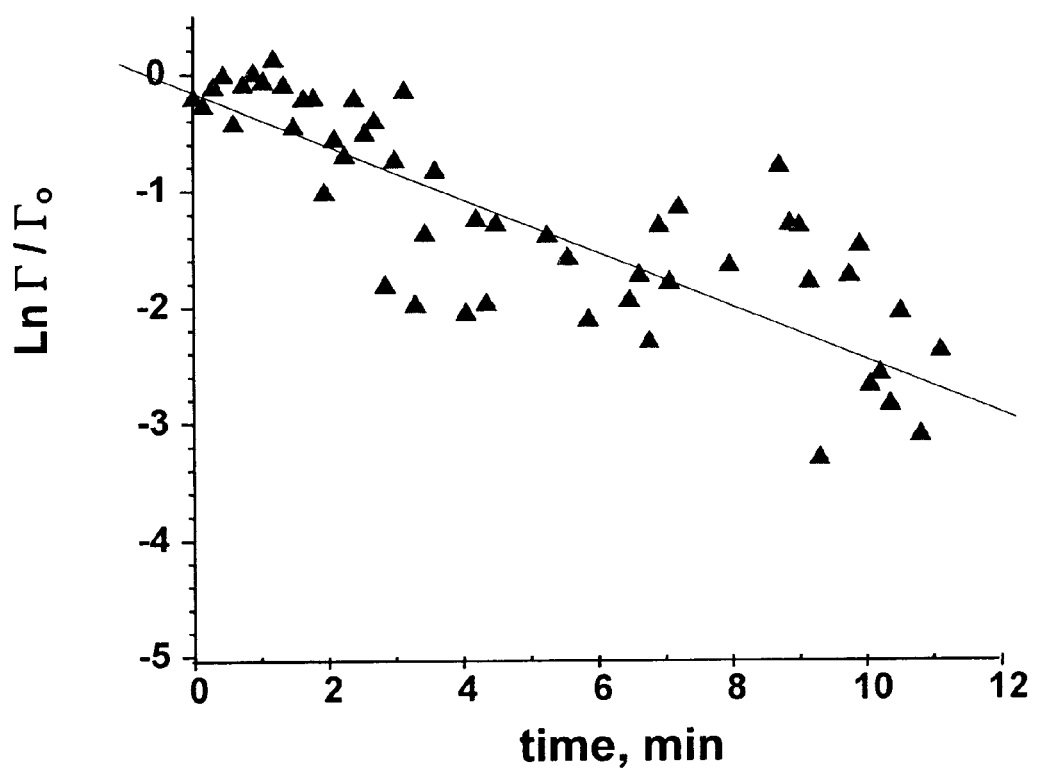
FIG. 12. Graphic representation of data showing reversible particle (1 μm silica) adhesion. More than 99% of the particles (I=0.026M) can be removed or displaced from a 10% positive patch/component surface.

Another interesting observation for the data in FIG. 4 is that in the limit of slow particle adhesion (for average positive domain densities of about 15% and below), the particle adhesion was reversible. That is, for the most negative surfaces to which particles adhered, they could be washed off in a matter of minutes simply by flowing pH 6 buffer (with I=0.005M). This observation is consistent with the concept of domain density-dependent adhesion and de-adhesion rate constants for the particles: Particle adhesion onto more positive surfaces is characterized by a relatively large adhesion rate constant and apparently irreversible adhesion (slow deadhesion rates). The more negative the surface, the slower the forward adhesion reaction and the more accessible the deadhesion kinetics. Reference is also made to FIG. 12, a graphic presentation of data showing reversible particle adhesion over time.

Figure 5:
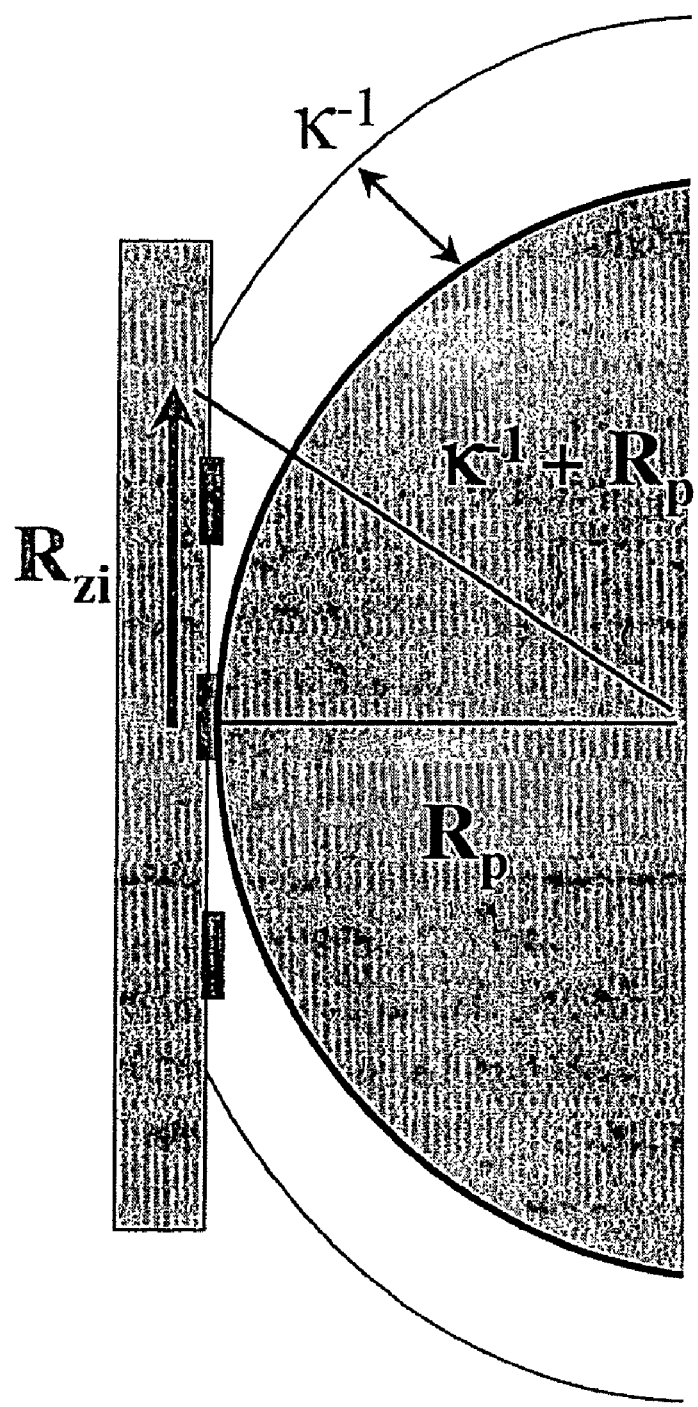
FIG. 5. Schematic illustration portraying a Zone of Influence and its radius, $R_{zi}$. Here a sphere of radius $R_p$ contacts the patchy planar surface, during conditions give a Debye length, $\kappa^{-1}$. $R_{zi}$ is calculated according to right triangles: $R_{zi}^2+Rp^2=(R_p+\kappa^{-1})^2$ FIG. 6. Effect of ionic strength on threshold for 1 μm particles.

Considering the concept of a threshold surface lengthscale, FIG. 5 illustrates another factor which can determine whether or not a particle will adhere to a heterogeneous surface: e.g., the lateral area on a collector surface with which a particle interacts as it approaches a surface. FIG. 5 can be viewed as an illustration to estimate the maximum size of this "zone of influence" (on the collector), based on electrostatics. Consistent with this particular embodiment, a particle is placed in hard contact with the surface, and the zone of influence is defined as the area on the planar surface that is intersected by an imaginary shell around the particle, corresponding to the Debye length; that is, a "zone of influence" of radius $R_{zi} = [(R_p + \kappa^{-1})^2 - R_p^2]^{1/2}$. For a particle size of 460 nm and a Debye length of 4 nm (corresponding to I=0.005M buffer) $R_{zi}$=43 nm. Alternately, include the Debye layer near the planar surface in the calculation: If the intersection of the Debye layers of the sphere and the planar surface are considered, $R_{zi}$=62 nm. The two estimates are the same within an order 1 multiplicative constant.

Regardless of how the zone of influence is defined, its radius approaches the average spacing between the domains at the adhesion threshold ($R_{zi}$=40-60 nm, average patch spacing 30 nm), further supporting the idea that spatial fluctuations in the domain arrangement govern particle adhesion. If one considers a circle of radius $R_{zi}$ (43 nm as an example) on the collector, one calculates an average of 5.5 domains in this zone at the adhesion threshold of 11% domains. Each domain carries a net 28 positive charges (this calculation includes the effects of counterion release on adsorption and of charge regulation, the localized increase in the underlying silica in the region of the patch). Despite the presence of these 7 domains in a 5800 nm² zone of influence, the average surface character is substantially net negative. In fact, 25 domains would be required to completely neutralize the zone of influence. If one assumes that particle adhesion requires at least a net neutral region of the surface, then at the adhesion threshold, particles adhere to localized regions with more than 3-4 times the average positive domain density. As the radius of the "zone of influence" approaches the average inter-patch spacing (at the adhesion threshold), such fluctuations become more probable, compared to the situation, for instance, when the zone of influence is much larger or smaller than the average domain distance.

As discussed above, nanometer scale surface features can be tuned to manipulate the adhesion of micron-scale objects. An appropriate lengthscale to be considered is not necessarily the particle size but the size of the interactive zone between the sphere and the plate, compared with the scale of the features on the planar surface. Thus, the local curvature can dominate the overall particle size, as alluded to in FIG. 1C. For the electrostatic system studied here, these lengthscales are well defined and approach each other at conditions the adhesion threshold. The presence of an adhesion threshold, gives rise to use of this invention for selective adhesive behavior, as is illustrated below in a specific example.

Figure 6:
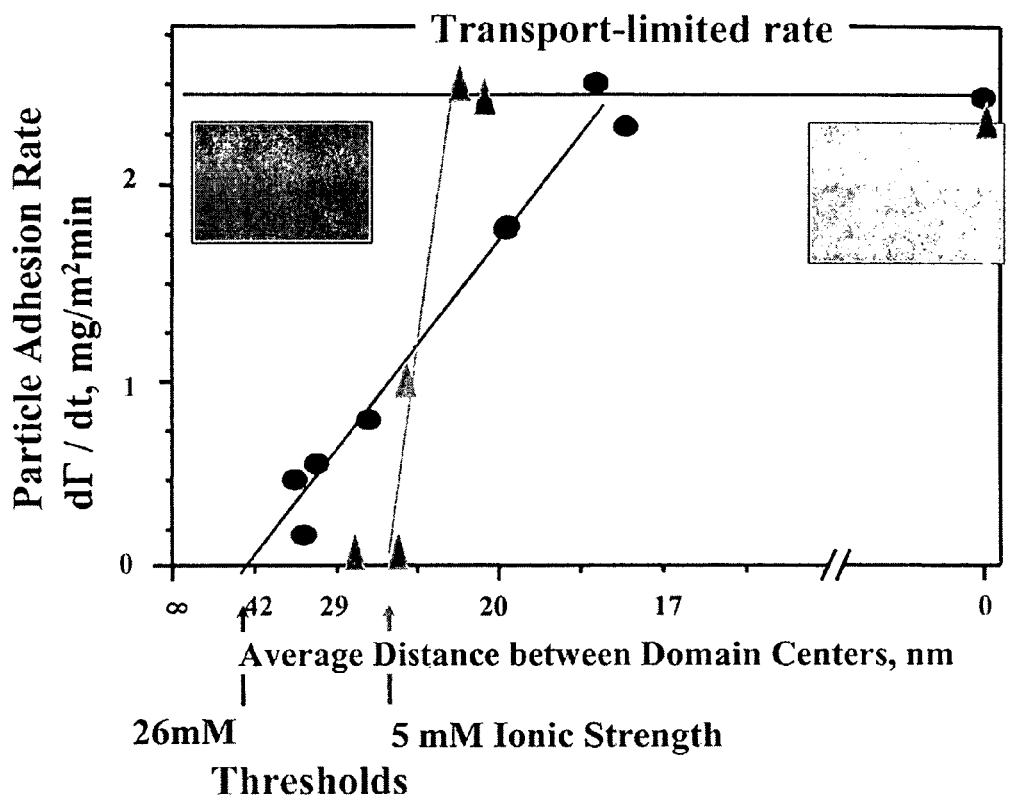

Reduction of solution ionic strength (or, e.g., a fluid medium carrying particles) to increase the Debye length and hence $R_{zi}$ finds the threshold shifted to higher average densities of positive domains, as shown in FIG. 6. (A similar behavior is observed for particle size variations, based on the definition of $R_{zi}$). Larger zones of influence more nearly reflect the average collector properties (net negative charge) while small zones of influence reflect its positive concentration fluctuations, the basis for size selectivity even without patterns on the particles. (Patterned particles, such a those in FIG. 1B, would experience an even more dramatic selectivity.) The influence of ionic strength confirms the concept of an electrostatic zone of influence and that the modified surfaces of this invention can discriminate particles by size or charge density. FIG. 6 highlights the region of selective adhesion for particle size, via $R_{zi}$, tunable through ionic strength.

Selectivity

With reference to examples 5a-b, below, charge-wise heterogeneous surfaces were generated with % positive domains corresponding to case i and case ii in FIG. 10A. The two surfaces were then exposed to flowing suspensions containing 65 wt % (with respect to silica content) 460 nm fluorescent-core plain shell silica particles and 35 wt % (with respect to silica content) 1 μm non-fluorescent (pure) silica. The 460 nm particles had been centrifuged and resuspended by mixing and ultrasonication, as part of their synthesis/purification procedure and, as a result of incomplete resuspension, the 460 nm particle portion of the mixture contained a small amount of aggregates of the 460 nm primary particles. This included some doublets and triplets, but also aggregates several microns in size. In the supply container which fed the flow chamber, these aggregates were the largest particles present and settled to towards the bottom of the container faster than the primary 460 nm and 1 μm particles. When the tube which fed the flow chamber was immersed deep into the supply container, these aggregates were pumped into the flow cell along with the primary particles.

The micrograph of FIG. 11A shows the surface for case i after exposure to the mixture containing 460 nm fluorescent spheres, 1 μm non-fluorescent particles, and aggregates of the 460 nm particles. Here only the 460 nm particles and aggregates thereof adhered to the surface, while 1 μm particles were rejected, indicating the case i surface was selective for 460 nm spheres and larger objects having local curvature corresponding to 460 nm. The 1 μm particles which were rejected by the case i surface were hydrodynamically and mass-moment smaller than the aggregates of the 460 nm particles, yet they were rejected by surface because of their larger radius of curvature.

The micrograph of FIG. 11B shows the control run for this study, using the case ii surface. This surface captured all types of particles (460 nm and 1 μm primary particles, and aggregates of the 460 nm particles) injected into the flowcell. While FIG. 11B is a light micrograph which shows all the particles on the surface, switching to fluorescent light made the 1 μm spheres invisible, proof that both sized particles adhered, as expected.

These results illustrate the selectivity of the charge-wise heterogeneous surfaces, favoring adhesion of smaller objects or complex objects with small radii of curvature, while rejecting large smooth spheres possessing greater radii of curvature.

Dynamic Signatures

In addition to the ability to control the adhesion rates and adhesion reversibility of particles using heterogeneous surfaces, preliminary optical microscopy studies revealed interesting dynamic signatures. Substantially positive collector surfaces produced irreversible particle adhesion; however, moderate domain spacing yielded reversible adhesion with single exponential detachment kinetics and $\tau$=50-500 s. In the reversible regime, particles rolled or skipped as they first encountered the surface, reminiscent of neutrophil (a type of white bloodcell) interactions with the endothelium. Adhesion at an injury occurs by rolling, mediated by the forming and breaking of selectin-carbohydrate bonds. Arrest follows as integrins bind more tightly. Without selectins to first reduce the neutrophil velocity, integrins do not bind. By analogy, dynamic signatures associated with this invention can comprise any one or a combination of adhesion, rolling, arrest and the like. Indeed, with controlled chemistries and distributions of features, sensor surfaces can distinguish the approaching surfaces of bacteria having size and charge characteristics comparable to the silica spheres utilized herein, based on the signature of their interfacial motion, leaving an active (not spent) sensing area.

Detection Schemes

Detection can employ TIRF, optical reflectometry, and microscopy to evaluate particle adhesion and, in the reversible regime, particle detachment. All characterization for particles and surfaces can be conducted as needed by available methods described herein or as otherwise known in the art. In addition to material variations (particle and collector chemistries, domain dimensions and density, charge density) that affect the interplay of colloidal forces, systematic flow rate variations can produce adhesion signatures such as rolling, skipping, and arrest. Particle motion can be quantified with optical microscopy using a horizontal flow chamber that avoids the domination of interfacial forces by gravity. Further, studies can employ existing steady shear flow chambers that provide a uniform wall shear rate and an additional flow cell geometry, with an increasing chamber cross section, to spatially vary shear in a single experiment, probing critical conditions for particle arrest. Experiments and theory target the limit of low particle coverage, relevant to high sensitivity, early detection, and adhesion fundamentals.

Figure 7:
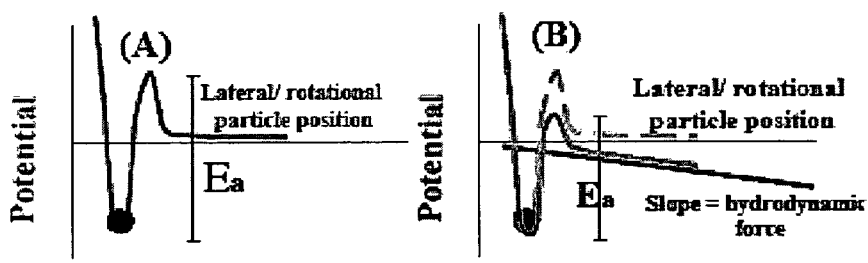
FIGS. 7A-B. (A) Activation energy follows from colloidal potential (B) Activation energy follows from additive colloidal and hydrodynamic potentials.

Adhesion can be analyzed as described herein, where TIRF and reflectivity signal was proportional to the instantaneous amount of particles adhering to the detector. In the low particle coverage limit, with strong (irreversible) adhesion onto highly attractive surfaces, the forward adhesion rate law can be assessed when the mass transport rate is sufficiently large. In the reversible regime (with less attractive surfaces), the removal (in flow) of previously adhering particles can reveal the detachment rate law. The rate laws, likely first order, can depend on the particle concentration while the rate constants $k_{on}$ and $k_{off}$ can depend on a system's "chemical-force" parameters (collector surface chemistry and patchiness, choice of particle, ionic strength and flow rate). The latter control the colloidal interaction of the particle with the surface landscape. Maxima in these potentials should act as activation energies, $E_a$, per FIG. 7 and establish the rate constants via Kramer's rate theory: $k=\omega e^{Ea/kT}$. The attempt frequency, $\omega$, can, in principle, be determined by temperature variations; however, temperature is a thermodynamic parameter (e.g. affecting solvent quality) not merely a dynamic one. Therefore, the ionic strength, which varies the electrostatics in ways that are known, can systematically vary the potential barrier, decoupling $\omega$ and $E_a$. External forces such as hydrodynamics add to colloidal potentials to reduce the barrier height and produce velocity-dependent rate constants, a treatment to be used, per FIG. 7B.

When particle rolling and skipping occurs, direct measurement of $k_{on}$ and $k_{off}$ is complicated, because bonds simultaneously form and break at the leading and trailing edges of the zone of influence. In this regime, $k_{off}$ can be measured in detachment experiments that follow deposition of a small amount of particles onto a surface in a preconditioning step. Microscopy can confirm the extent to which particles can be removed or roll in different shear flows. $K_{on}$ can follow from measurements of the steady-state (equilibrium) particle density on the surface. With weak binding, this equilibrium particle coverage should be quite low. Measurements of rolling velocities (and distributions thereof) and any rolling or skipping prior to final arrest can be measured, and interpreted in the context of a model which includes the probability of particles encountering favorable patches at their leading edges.

EXAMPLES OF THE INVENTION

The following non-limiting examples and data illustrate various aspects and features relating to the systems and/or methods of the present invention, including the use of heterogeneous surfaces having various spatial components/arrays as are available through the fabrication techniques described herein. In comparison with the prior art, the present systems and methods provide results and data which are surprising, unexpected and contrary thereto. While the utility of this invention is illustrated through the use of several such surfaces and particles interacting therewith, it will be understood by those skilled in the art that comparable results are obtainable with various other patterned heterogeneous surfaces and interacting particles, as are commensurate with the scope of this invention.

PDMAEMA with a molecular weight of 31,300 and a polydispersity of 1.1 was a gift from DuPont, supplied in a THF solution. Rotary evaporation was used to replace the original THF solvent with water. Final sample purity was confirmed via proton NMR spectroscopy. A handful of control runs tracking the presence (and lack of removal) of positively charged pDMAEMA surface domains employed a lightly rhodamine-b-tagged version of pDMAEMA. The labeling procedure has been described previously, and in the current study, the labeling density was 1 label/13 chains. Of note, rhodamine was found to be noninvasive in mobility studies of pDMAEMA on silica. (See, Hansupalak, N.; Santore, M. M. Macromolecules 2004, 37, 1621-1629.)

The planar substrates were the surfaces of microscope slides (Fisher Scientific, Pittsburgh, Pa.) which had been treated with sulfuric acid and rinsed in a sealed flow cell to produce a pure silica surface, free from contamination by airborne organics. Previous XPS studies confirmed the removal of sodium, calcium, and other salts from the region near the surface, leaving the exposed silica layer. This silica layer, measured optically, is on the order of 10 nm thick, with a refractive index of 1.49.

pH 6.1 (±0.05) buffer solutions (with I=0.026M) were made using 0.0234 M $KH_2PO_4$ and adding a very small amount of 0.000267 M NaOH. This solution was diluted as necessary to achieve the dilute buffer concentration (I=0.005M) in this work. Negligible effect of buffer concentration on pH was found in the range (0.005-0.1M), and neither acid nor base were added for further pH adjustment.

Example 1a

Charge-wise-heterogeneous planar surfaces were generated by adsorbing varied amounts of pDMAEMA onto these silica surfaces from a 20 ppm flowing pH 6.1 buffered solution (at ionic strength, I=0.026M), using a laminar slit flow cell with a 10×40 mm slit machined into a black Teflon block and sealed against the microscope slide substrate using an o-ring. Continuous gentle flow (with wall shear rates in the range 10-50 $s^{-1}$) maintained a constant bulk solution concentration and defined the mass-transport conditions. Saturated (completely positive and overcompensating the underlying silica substrate) surfaces were generated by allowing the pDMAEMA to adsorb for a few minutes longer than needed to saturate the surface. To generate heterogeneous surfaces, adsorption from gentle shearing flow was allowed to proceed only for a few seconds (a time which was systematically varied to tune the domain density) before the flow was switched back to pure buffer. Adsorbed pDMAEMA chains were aged in this buffer for 10 minutes before exposure to silica particles in adhesion tests, a time period found to yield fully relaxed pDMAEMA layers (eliminating any potential history dependence).

Example 1b

With reference to the preceding example, various other cationic polyelectrolytes can be physically adsorbed to a negatively charged surface, silica or otherwise, to provide other heterogeneous surfaces in accordance with this invention. Likewise, such charged components can undergo further chemistry for covalent attachment to such a surface member. Alternatively, spaced components comprising one or more available anionic polyelectrolytes can be employed on a positive surface member (e.g., a cationic self-assembled monolayer) for a reversed charge configuration. While planar silica slides were used as a negative surface member/substrate, the systems and methods of this invention can be employed with other oxide surfaces or, likewise, with non-planar surface/substrate configurations, for instance, the surfaces of fibers. For instance, a positively charged surface member can be constructed from a coating or monolayer of a material such as aminopropyltriethoxysilane coupled or applied to a suitable substrate. Negatively charged spaced components can comprise an anionic polyelectrolyte such as but not limited to polyacrylic acid. The effectiveness of such a heterogeneous surface can be demonstrated using cationic latex to simulate sensing a positively charged particle. Other such heterogeneous surface constructions are as would be understood by one skilled in the art made aware of this invention, such surfaces as can be employed according to the methods and systems described herein.

Example 2

Monodisperse silica particles serve as an analyte, to exemplify the workings of the invention. Microscopy and optical reflectometry detection methods sense all silica particles utilized, while total internal reflectance fluorescence and fluorescence microscopy require fluorescent silica particles. In the case of fluorescent particles, they were synthesized such that a fluorescent dye resides in the core of the particle. The outer shell of the silica particle contains no dye and presents a pure silica surface (with negative charge) to the surrounding fluid. The fluorescent cores of some samples of particles allowed them to be distinguished from other, non-fluorescent particles that were added to the analyte suspension in some of the examples below.

To synthesize colloidal silica particles with fluorescent cores, a modified Stober process was used. (See, Vanblaaderen, A.; Vrij, A. *Langmuir* 1992, 8, 2921-2931; Stober, W.; Fink, A.; Bohn, E. *Journal of Colloid and Interface Science* 1968, 26, 62-&.) Tetraethoxysilane (TEOS, Sigma) was freshly distilled before the synthesis to remove all the aggregates; (3-aminopropyl)triethoxysilane (APTS, Aldrich) was used without purification. Ethanol (200 proof, VWR), and ammonium hydroxide (Sigma-Aldrich, 25%, analytical reagent quality) were filtered through 0.2 μm filters to remove dust prior the synthesis. In the first step, which produced a "dye precursor," Rhodamine B isothiocyanate (Sigma), was covalently attached to APTS by mixing the two in anhydrous ethanol (with 25% excess of APTS) and allowing them to react under the nitrogen flow for at least 12 hours. In the second step, seed formation, freshly-made dye precursor was added to an ammonia-ethanol mixture along with TEOS and stirred gently for 10 hours. Four steps of growing were then done, adding same amount of TEOS and allowing mixture to react for at least 8 hours for each step, to progressively place shells of untagged silica over the core. After that, particles were gently centrifuged to remove supernatant with unreacted dye and APTS and washed with ethanol 2 times. Next, rinsed particles were re-suspended in an ethanol-ammonia mixture and another 4 growth steps were performed. Particles were then washed 4 times with ethanol, and 7 times with water. Particles size was characterized using SEM and DLS. Both methods gave similar results—a diameter of about 460 nm and a low polydispersity of 1-2%.

Example 3

Total internal reflectance fluorescence was used to measure the adhesion rates of the fluorescent-core silica spheres and, in control studies employing fluorescent pDMAEMA, polymer adsorption. A TIRF cell inside a Spex Fluorolog II spectrometer was employed, as previously described in the literature. Excitation light was at 553 nm and emissions were measured at 573 nm. An evanescent penetration depth near 100 nm, in our instrument, easily excites labels on a nanometer-thin layer of adsorbed polymer, but it also is highly effective to excite the cores of 460 nm silica particles. Though an evanescent wave with a decay length of 100 nm would appear not to be able to reach into the core of an interfacially adhesive half-micron silica sphere, evanescent light can traverse a thin gap of low refractive index to tunnel into a higher refractive index medium. The evanescent wave tunnels into the sphere and scatters, exciting the rhodamine containing core. Indeed, fluorescence signal from interfacially adhesive rhodamine-core silica particles was some of the largest in our experience with TIRF.

Example 4a

The data of this example demonstrate several principles supporting the utility of this invention; that is, various particle/surface interactions.

Figure 8A:
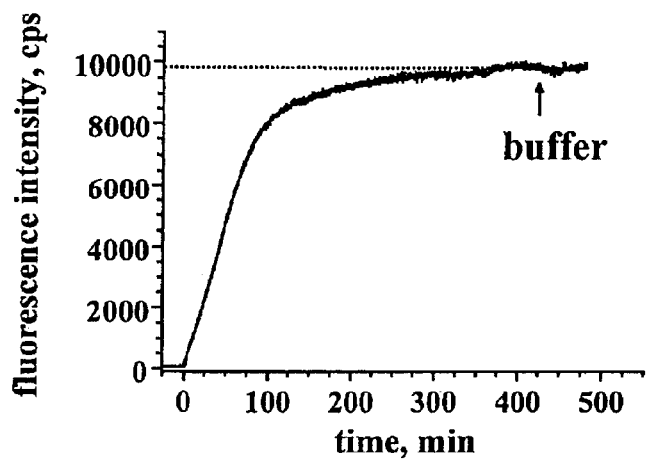
FIGS. 8A-C. One method of measuring particle adhesion rates to surfaces (heterogeneous and otherwise) is Total Internal Reflectance Fluorescence (TIRF). Shown here are TIRF data for the adhesion of 460 nm Rhodamine-core silica spheres having, negative surfaces, onto a planar surface made positive by a saturated layer of pDMAEMA. (A) Continued particle deposition for several hours until the particle deposition rate is substantially reduced by surface crowding. The bulk particle concentration is 0.1 wt % and the wall shear rate is 39 s$^{-1}$. (B) Initial deposition kinetics at the same wall shear rate and different bulk particle concentrations. The inset shows explicit dependence of the deposition rate on the particle concentration. (C) Control runs showing the particle adhesion rate onto a surface made uniformly positive by pDMAEMA saturation is independent of bulk ionic strength in the range 0.005-0.026M, and also that there is no particle adhesion onto bare silica for this batch of 460 nm spheres. Here, buffer is reinjected after 20 minutes of particle deposition.
Figure 8B:
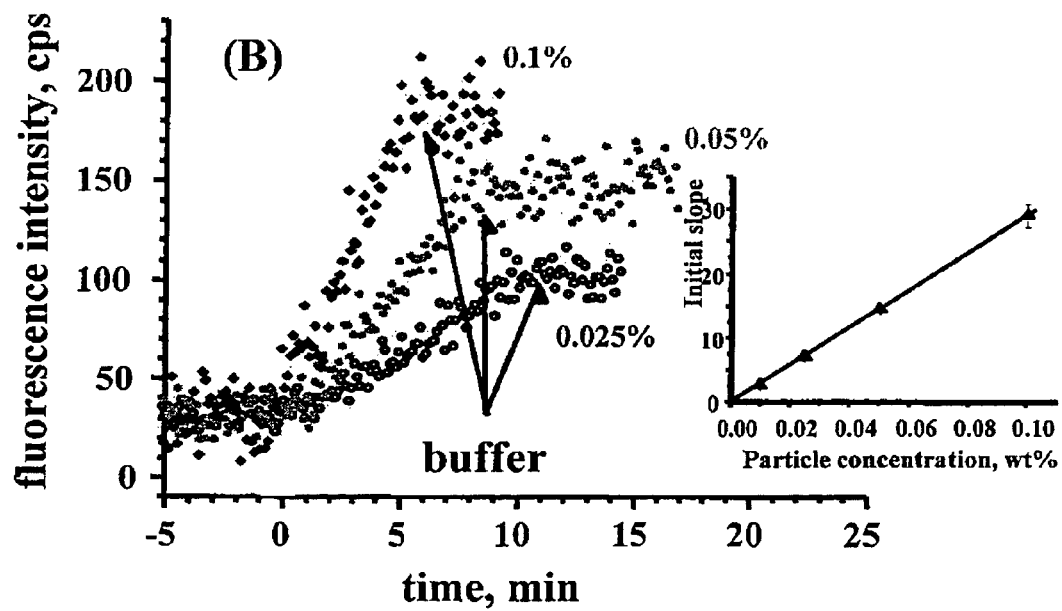
Figure 8C:
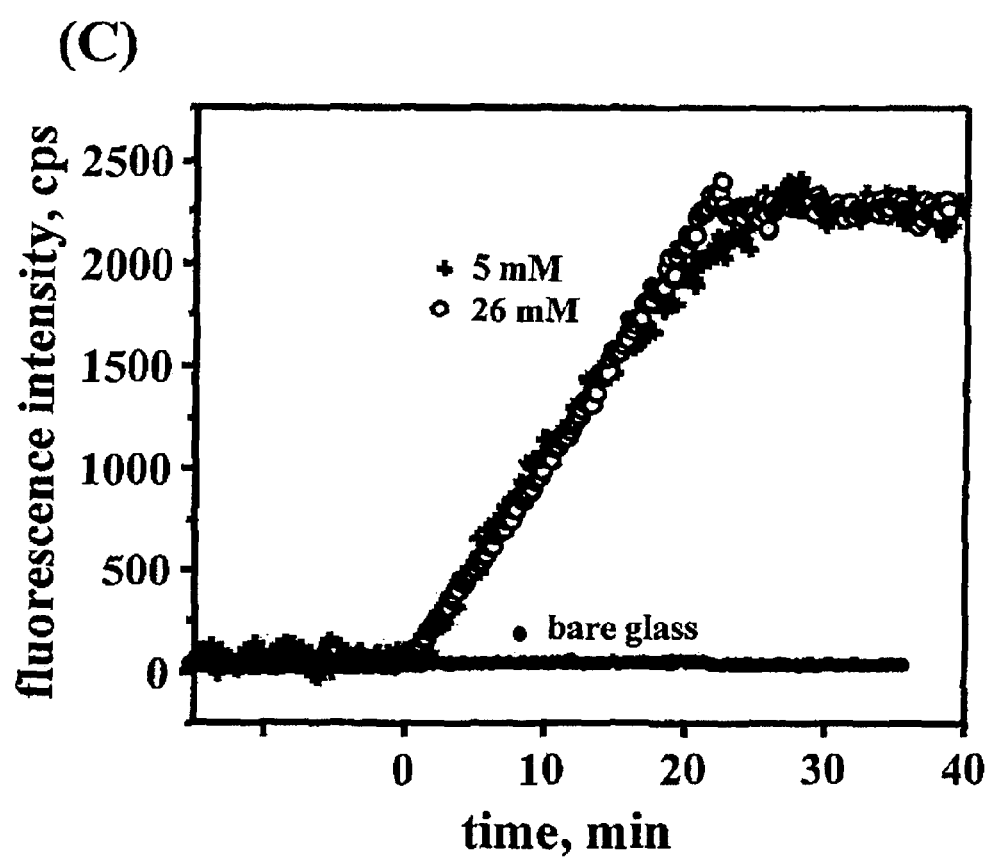

The non-fluorescent layers of pDMAEMA were deposited prior to the introduction of fluorescent silica particles at time zero. Control studies with fluorescent pDMAEMA to confirm that no polymer was removed during interaction of the layer with particles from solution. FIG. 8A presents TIRF data for the adhesion of the 460 nm fluorescent-core silica spheres on the fully adhesive fully positive, attractive (saturated pDMAEMA) surface. With a bulk concentration of 0.1 wt % and a wall shear rate of 39 $s^{-1}$, particle adhesion is initially linear in time, but levels off within 5 hours. Towards the end of the run, pure pH 6.1 buffer was injected and the particles were not rinsed off the surface, indicating irreversible (for practical purposes) adhesion. Particles could not be removed even when the ionic strength was raised to 1M or DI water was introduced. FIG. 8B further explores the initial particle adsorption kinetics onto saturated pDMAEMA layers, focusing on the influence of particle concentration. In each of these runs, buffer is injected at the arrows and the lack of signal drop indicates particle retention on these surfaces. In the inset it is clear that the initial adhesion rate increases in linear proportion to the bulk particle concentration, one of the signatures of transport-limited deposition. FIG. 8C demonstrates that the initial (limiting low particle coverage) particle deposition rate is independent of ionic strength (in the range 0.005-0.026M). (This was also true of the initial pDMAEMA coverage, which is not shown.) Also in FIG. 8C, another control experiment is shown: The silica particles do not adhere to acid etched slides not carrying pDMAEMA. This confirms the repulsive interaction between a bare collector surface and the silica particles. (This result is non-trivial as several batches of silica particles from commercial sources failed this test.)

Example 4b

Figure 9:
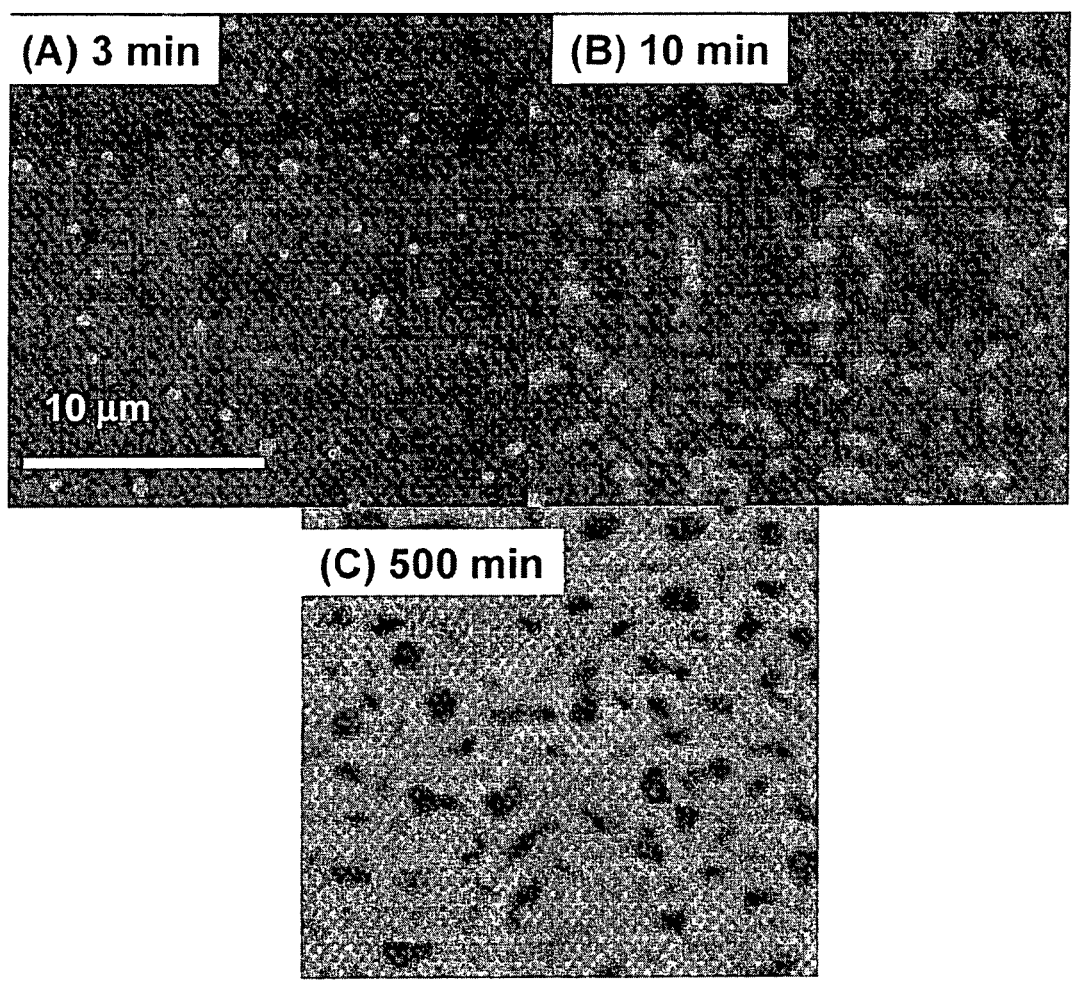
FIG. 9. Optical micrographs of 460 nm particles adhering to fully positive collectors, for runs like that in FIG. 3A, but interrupted at different times for optical microscopy: (A) 3 minutes (B) 10 minutes and (C) 500 minutes. Note that the dynamic signatures and recognition of target particles/analyte by heterogeneous surfaces can be observed at particle levels much lower than exemplified here with optical microscopy.

FIG. 9 presents optical micrographs of surfaces generated in runs like that in FIG. 8A. After in-situ cleaning and rinsing of the microscope slide in the flow cell, a saturated pDMAEMA layer was deposited from a bulk solution of 85 ppm and a wall shear rate of 39 $s^{-1}$ (at pH 6.1 and an ionic strength of 0.026M). After 10 minutes, the layer was exposed to pure buffer for another 10 minutes. Next, a 0.1 wt % dispersion of 460 nm silica spheres was passed over the surface for the times indicated in parts A-C of FIG. 9, after which the flow was switched back to buffer to remove the free particles from the bulk solution. During this final buffer rinse, no particles were removed from the surface, as evidenced by a lack of fluorescence signal drop. At this point, the TIRF cell was carefully dismantled and the microscope slide dried and moved to an optical microscope to record the image at the central observation point (corresponding to the mass transfer conditions in the active TIRF area). FIG. 9 therefore shows the adherent particles, for different times in the run of FIG. 8A.

In FIGS. 9A-C, it is clear that the silica particle coverage increases substantially with increased particle deposition time, as expected. Also of note is the random arrangement of particle deposition and lack of colloidal ordering, though some doublets are present. At long times (in FIG. 9C) there is no evidence for multilayer formation and, indeed, none would be expected since the flow cell is oriented vertically, so that gravity does not aid deposition. At short times (i.e., FIG. 9A), it was possible to count the adherent silica particles. For the run at 3 minutes, we counted a total of 236 particles per 40×50 μm square (40×50 um$^2$ is the full field, only close-ups are shown in FIG. 9), which corresponds to a silica particle coverage of 13.2 mg/m$^2$.

Example 5a

A comparison was made of the adhesion rates of monodisperse 460 nm and 1000 nanometer silica particles onto several series of heterogeneous surfaces, whose domain density is varied as shown on the x-axis. See FIGS. 10A-B. (100% domain density corresponds to a saturated uniform layer of pDMAEMA which carries substantial positive (attractive) charge). In general, on the right side of each of these graphs where the collecting surfaces are predominantly pDMAEMA, the particles adhere quickly since the collecting surface charge is net positive while the particles are negative. 50% patches corresponds to a net neutrality of the collector surface, though locally there are positively and negatively charged regions. With less pDMAEMA positive domain loading on the surface (greater spacing between the domains), the adhesion rate generally slows and in all cases the adhesion rate goes to zero at a positive x-intercept.

As discussed above, that the data do not pass through the graphic origin suggests that more than one domain or surface component is needed to trap each particle on the surface. The x-intercept for each data set corresponds to an average surface domain density that acts as a threshold below which no adhesion occurs. Note that this threshold (and the specific particle adhesion rates) depends on particle size and charge density, a basis for particle selectivity. The threshold below which no adhesion occurs is consistent with the concept of pattern recognition illustrated in FIG. 1.

To demonstrate selectivity, two heterogeneous component surfaces, designated by the lines "case i" and "case ii" in FIG. 10A, were exposed to a mixture of 460 nm and 1000 nm particles (65 and 35 wt %, respectively), which also contained aggregates of the 460 nm particles. Line i passes through the data curve in FIG. 10A for the 460 nanometer particles with a finite adsorption rate of 0.75 mg/m$^2$/min, but the adhesion rate of the 1000 nm particles for the same conditions on the same surface is zero. Therefore only 460 nm particles should adhere. Line ii corresponds to a surface with a greater density of surface domains, acting as a control. Here there are finite, albeit different adhesion rates of both particles.

Example 5b

Optical microscopic images (FIGS. 11A and 11B) were also obtained for surfaces exposed to a mixture of particles as illustrated in FIG. 10A at lines (i) and (ii). For (i), after a half-hour exposure to the particle mixture, only the smaller particles (460 nm) and aggregates thereof adhered to the subject surface—demonstrating selectivity of this surface for the smaller particles or species of small local curvature. (See FIG. 11A.). In contrast, for (ii), both the smaller particles and aggregates of the smaller particles and larger (1000 nm) particles adhere. (See FIG. 11B.) There are substantial numbers of the larger particles on this surface. Such results were confirmed using fluorescence microscopy: the smaller particles contained fluorescent cores and were apparent; the larger particles were not fluorescent, but appeared as dark spots in the fluorescence image. The surface of case ii indiscriminately captured both the larger and smaller particles, again demonstrating selectivity can be engineered by controlling the average spacing of surface components on a collecting surface member. Reference is made to the preceding discussion regarding the presence and generation of particles (e.g., 460 nm), aggregates (e.g., 1000 nm), aggregates of the smaller particles (e.g., greater than 460 nm) and mixtures thereof.

Example 6

For interfacially adherent objects which act as Brownian diffusers in free solution, the Leveque equation can describe the transport-limited accumulation of these objects on a collector, dΓ/dt, from the steady state solution to the convection-diffusion equation in a slit shear cell:

$$\frac{d\Gamma}{dt} = \frac{1}{\Gamma(4/3)9^{1/3}} \left(\frac{\gamma}{DL}\right)^{1/3} DC_o. \quad (1)$$

Here, $C_o$ is the bulk solution concentration, γ is the wall shear rate, D is the bulk solution diffusivity, and L is the distance from the entrance to the point of observation in the cell. On the right side of equation 1, (and only there), Γ (4/3) is the gamma function evaluated for an argument of 4/3. Equation 1 was successfully applied to describe the adsorption kinetics of polymers and proteins in shear cells. Applying it to 460 nm silica particles (with a Stokes-Einstein-diffusivity of 1.062× 10$^{-8}$ cm$^2$/s), a deposition rate, dΓ/dt, of 0.0712 mg/m$^2$ s would be anticipated for the linear regime of FIG. 8A. At 3 minutes this corresponds to a coverage of 12.8 mg/m$^2$ which is in excellent agreement (less than 5% error) with the particles counted in the micrograph of FIG. 9A, 13.2 mg/m$^2$. Such results indicate that the adhesion rate of 460 nm particles on the positive collector is the transport-limited rate corresponding to a lack of energy barrier between the particle and the surface. The observations also confirm that the 460 nm particles are too small to exhibit hydrodynamic lift at the interface, which would tend to retard their adhesion. Thus the micrographs confirm that the maximum adhesion rate is obtained for these negative silica particles on the uniformly adhesive (positive) surface. With the calculation in Example 6, FIG. 9A provides an independent calibration for the TIRF instrument in runs such as those in FIG. 8.

Example 7

Using the transport limited regime as a measure of coverage, the ultimate coverage level on the plateau of FIG. 8A is approximately 0.42 g/m$^2$, which is substantially less than the coverages of 0.53 and 0.61 g/m$^2$ which correspond to square and hexagonal packing of 460 nm silica spheres on a planar surface. The coverages corresponding to the initial deposition kinetics are far below these levels, indicating that the initial adhesion kinetics of particles on the heterogeneous surfaces characterize the bare (single particle) interactions between the particles and the surfaces, per FIG. 1.

Example 8

Consistent with the foregoing, other tests employed ml-quantities of fluid containing 10$^8$ spheres/ml (~10$^{-4}$ volume fraction), a dynamic reading obtained within 3 minutes and, in the cases of reversible adhesion, clearing of the detector surface within 10 minutes. Experiments were conducted in a standard rectangular flow cell (1×3×0.05 cm), with a long inlet tube (large fluid hold up) and a standard peristaltic pump. Microfluidic techniques can reduce the volume to 0.2 ml or less. More dilute solutions can readily be detected but require longer times, according to a surface rate law, for instance transport-limited or first order kinetics which are proportional to the bulk concentration. Regarding sensitivity, near-Brewster optical reflectometry, was found to reliably detect of adhesion of silica particles (200-1000 nm) at surface concentrations as low as 1-micron particle per 250 um$^2$ of area, in water. Fluorescence based detection, for instance TIRF, depends on the density of fluorescent labels on the object or molecule studied. With 460 nm fluorescent core plain-shell silica particles, fluorescent signal was reliably obtained at and below 1 mg/m$^2$, corresponding to 1 particle every 110 um$^2$. A similar fluorescence signal with larger particles would correspond to one 1-μm particle every 1000 μm$^2$.

Example 9

Both the size and charge density within positive domains, and the charge density on the main negative surface can be adjusted to tune particle size- and surface-based selectivity. The cationic domains can be flat, in contrast with a second type of patch based on block copolymers. Here an adhesive tail can extend from the flat part of the domain, with the adhesion groups distributed differently along the tail, and with the potential of accommodating a polypeptide on the chain end. This adhesive tail can provide elasticity and extend the range of attraction during pull-off. Based on adhesion theory, it provides a means of controlling the dynamic signature of particles. In all cases, surface domain density can be varied through deposition methods while the domain size follows from polymer molecular weight.

Example 10

In addition to positive domains made from p-DMAEMA, various other domain compositions can be derived using known synthetic methods to produce polymers with a variety of structural chemical-physical traits, including the robustness needed for operation in a variety of aqueous or dry environments, and long term stability. As would be understood by those skilled in the art, a number of known synthetic procedures can be used to prepare homo-, hetero- or copolymeric materials comprising a wide variety of functional groups, over a wide range of molecular weights and polydispersities, as may be desired for use in conjunction with a particular substrate surface and/or end use application.

We claim:
1. A method for particle sensing, said method comprising:
providing a heterogeneous surface comprising a surface member and a plurality of components thereon, said components spaced about said surface member and having a density thereon;
exposing a particle to said heterogeneous surface, said particle differently interactive with said surface member and said spaced components; and
sensing interaction of said particle with said heterogeneous surface.
2. The method of claim 1 wherein each of said particle, surface member and spaced components comprise a net charge, said particle electrostatically interactive with said heterogeneous surface.
3. The method of claim 2 wherein said components have a charge density at least partially sufficient for selective particle interaction.
4. The method of claim 3 wherein said components comprise an average spatial density, said spatial density at least partially sufficient for selective particle interaction.
5. The method of claim 4 wherein said spatial density is varied for selective particle interaction.
6. The method of claim 4 wherein said particle has a dimension selected from a spherical radius and a localized surface radius of curvature.
7. The method of claim 6 wherein said spatial density is varied for selective particle interaction.
8. The method of claim 2 wherein said interaction comprises particle adhesion with said surface.
9. The method of claim 8 wherein the adhesion threshold is varied with ionic strength.
10. The method of claim 8 wherein said exposure comprises a mixture of particles.
11. The method of claim 10 wherein one said particle comprises a first radial dimension and a second said particle comprises a second radial dimension greater than first radial dimension, each said dimension selected from a spherical radius and a localized surface radius of curvature, said first particle selectively attracted to said heterogeneous surface, said spaced components comprising a spatial density at least partially sufficient for selective interaction with said first particle.
12. The method of claim 10 wherein the ionic strength is varied for selective attraction.
13. The method of claim 11 wherein said interaction selectively separates said particle.
14. The method of claim 1 wherein said particle is displaced, for another particle exposure to said heterogeneous surface.
15. The method of claim 1 wherein said interaction is selective for separation of said particle.

* * * * *